(12) United States Patent
Sugaya et al.

(10) Patent No.: US 8,759,090 B2
(45) Date of Patent: *Jun. 24, 2014

(54) STEM CELL BANKING SYSTEM (75) Inventors: Kiminobu Sugaya, Winter Park, FL (US); Angel Alvarez, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 62 days.

This patent is subject to a terminal disclaimer.

(21) Appl. No.: 11/554,059

(22) Filed: Oct. 30, 2006

(65) Prior Publication Data

US 2008/0102521 A1  May 1, 2008

(51) Int. Cl.
- *C12N 5/00* (2006.01)
- *C12N 5/07* (2010.01)
- *G06Q 30/00* (2012.01)
- *G06Q 10/00* (2012.01)
- *A01N 1/00* (2006.01)

(52) U.S. Cl.
USPC ........ 435/325; 435/365.1; 435/374; 435/377; 705/26.1; 705/26.8; 705/28

(58) Field of Classification Search
None
See application file for complete search history.

(56) References Cited

U.S. PATENT DOCUMENTS

| | | |
|---|---|---|
| 2003/0148513 A1 | 8/2003 | Sugaya et al. |
| 2003/0219898 A1 | 11/2003 | Sugaya et al. |
| 2006/0110440 A1 | 5/2006 | Sugaya et al. |
| 2006/0134789 A1 | 6/2006 | Sugaya et al. |
| 2006/0188489 A1 | 8/2006 | Sugaya et al. |

FOREIGN PATENT DOCUMENTS

| | | | |
|---|---|---|---|
| GB | WO 03/064463 A3 | * | 8/2003 |
| JP | WO 2004/072226 A3 | * | 8/2004 |

OTHER PUBLICATIONS

Tada et al., 2006, Neurodegener. Dis. 3: 32-67.*
Chambers et al., 2003, Cell 113:643-655.*
Takahashi et al, 2006, Cell 126:663-676.*
Yu et al.,2007, Science 318:19171920.*
STIC sequence search I, Mar. 9, 2011; pp. 1/1.*
STIC sequence search II, Mar. 9, 2011; pp. 1/1.*
Takahashi et al., 2006. Cell 126:: 663-676.*
Silva et al., Jun. 2006, Nature 44:997-1001.*
Hatano et al., Mechanism of Development, 2005, 122:67-69.*

* cited by examiner

*Primary Examiner* — Robert M Kelly
*Assistant Examiner* — Kelaginamane T Hiriyanna
(74) *Attorney, Agent, or Firm* — Timothy H. Van Dyke; Beusse, Wolter, Sanks, Mora & Maire, P.A.

(57) ABSTRACT

Disclosed herein are methods for producing a stem cell bank and providing stem cell samples for purchase or use. Also, provided herein are embodiments relating to a stem cell bank and stem cell banking system.

12 Claims, 3 Drawing Sheets

STEM CELL BANKING SYSTEM

BACKGROUND

Much research is being conducted to study stem cells and to devise ways of utilizing stem cells in treating various neurological diseases and injuries, as well as diseases and injuries of other organ systems. It is generally recognized that stem cell technologies hold tremendous promise for treating and ultimately curing neurologically related diseases, injuries or dysfunctions and those of other organ systems. However, despite the interest in stem cell research, scientists do not have a systematic system for obtaining stem cells for research purposes.

DETAILED DESCRIPTION

The subject invention is based on the inventors' realization that there is a need for a convenient systematic access to different stem cell lines. The inventors have realized that the ability to identify stem cell lines derived from somatic cells harvested from healthy subjects and subjects having known disease states or disease symptoms would be invaluable to researchers. Subjects may be human or nonhuman vertebrates. The inventors have developed methods of harvesting somatic cells, processing cells to increase their potency and cataloguing cells according to specific characteristics and traits.

For example, according to another embodiment, cells are harvested, catalogued according to predetermined characteristics, e.g., phenotypic information, morphological characteristics, differentiation profile, blood type, major histocompatibility complex, disease state of donor, or genotypic information (e.g. single nucleated polymorphisms, 'SNPs' of a specific nucleic acid sequence associated with a gene, or genomic or mitochondrial DNA), and stored under appropriate conditions (typically by freezing) to keep the stem cells alive and functioning. Cataloguing may constitute creating a centralized record of the characteristics obtained for each cell population, such as, but not limited to, an assembled written record or a computer database with information inputted therein. Essentially, this embodiment pertains to the production of a stem cell bank. The stem cell bank facilitates the selection from a plurality of samples of a specific stem cell sample suitable for a researcher's needs. Thus, another embodiment of the subject invention pertains to a stem cell bank comprising a plurality of stem cells samples obtained from separate sources and which are characterized and catalogued according to at least one predetermined characteristic. An additional embodiment pertains to a method of establishing a stem cell bank comprising collecting stem samples from multiple sources; cataloguing the samples according to at least one predetermined characteristic and storing the cells under conditions that keep cells viable.

According to a specific embodiment, the subject invention pertains to a stem cell banking system comprising a plurality of stem cell populations disposed in individual containers under conditions to keep said stem cell populations viable; a database computer comprising at least one processing module, a display, and a storage medium comprising information of at least one characteristic for each of said stem cell population; and at least one program code module for causing said information to be viewable on said display upon command by a user. In a specific embodiment, the invention pertains to a stem cell banking system wherein the stem cell populations comprise stem cells obtained from subjects who have a disease condition. The disease condition may include, but is not limited to, cardiovascular disease, cancer, neurological disease, such as Alzheimer's disease, Parkinson's disease, Huntington's Chorea, Lou-Gherig's disease, etc. Stem cells are harvested from different subjects having a different disease, and the stem cells are characterized. The characteristic(s) is/are inputted into the database computer. In addition, or alternatively, cells are characterized based on a specific phenotype not necessarily associated with a disease condition. For example, not to be construed as limiting, liver cells can be characterized based on their ability to metabolized certain compounds such as caffeine, alcohol, drug agents, etc. to study genetic bases of such different metabolism abilities, or underlying physiology associated therewith. Other types of cells can be characterized based on functional and/or morphological phenotypes.

Examples, include, but are not limited to, mesenchymal stem cells (MeSCs), neural stem cells (NSCs), hematopoietic stem cells (HSCs), fibroblasts or endothelial cells. Population of stem cells can be derived from a number of different sources. Stem populations useful in conjunction with certain embodiments described herein include, but are not limited to, brain-derived neural stem cells, bone marrow derived mesenchymal stem cells, adipose-derived mesenchymal stem cells, blood-derived hematopoietic stem cells, cord-blood-derived stem cells.

In certain embodiments, the harvested cells may be subjected to conditions to influence differentiation or dedifferentiation through introduction of engineered vectors, or other genetic material. Dedifferentiation comprises the manipulation of a cell such that it takes on the properties of a less differentiated cell. U.S. application Ser. Nos. 11/258,401; 11/258,603; 11/258,392 and 11/258,360 discuss various methods for biasing potency and/or differentiation of stem cells, and are incorporated herein by reference.

In a specific example, adult somatic cells including but not limited to white blood cells, fibroblasts, mesenchymal stem cells, and skin cells can be treated with nucleotide derivatives such as BrdU or 5-azacytidine to epigenetically modify the cells to increase their developmental potential. Additionally, cells can be treated with genes that expand the potency of cells including but not limited to genes that are responsible for maintaining the properties of embryonic stem cells such as nanog.

Cells can be positively selected for using cell-specific markers including but not limited to CD34, CD133 (hematopoietic stem cells), STRO-1, SH2, SH3, (mesenchymal stem cells), nestin, PSA-NCAM (neural stem cells). Cells can also be purified through negative selection by selecting out cells that express markers not present in the desired cell population. For example, lineage markers indicating differentiation such as CD38, CD45, and "Lin" markers (blood cell lineage proteins expressed in differentiating blood cells) can select out white blood cells from a mixture of cells.

Cells can also be selected using physical properties such as growth characteristics, adhesion, and/or density. For example, a density gradient can separate red blood cells from a solution of bone marrow and adhesion of cells to a culture flask can select for mesenchymal cells (while hematopoietic cells remain non-adherent).

As discussed above, stem cells may be procured using convention techniques in the stem cell art. In one example, stem cells are obtained from bone marrow or blood. See, for example, Friedenstein A J, Gorskaja J F, Kulagina N N, *Exp Hematol.* 1976 September; 4(5):267-74; and Caplan A I J, *Orthop Res.* 1991 September; 9(5):641-50. A bone marrow sample is explanted from a donor and hematopoietic stem cells are isolated from the marrow sample according to known techniques, including use flow cytometry or an affinity column. See, for example, U.S. Patent Publication Nos. 20040265996; 20050158857; 20060088890; and 20060073124. In a specific embodiment, hematopoietic cells are isolated using positive or negative selection. See U.S. Patent Publication No. 20060073124. Negative selection removes unwanted cells using certain markers such as C45 or positive selection using CD34.

Once cells are isolated they may be cultured, expanded, subjected to external biasing factors and/or genetically modified by introduction of genes encoding for biasing factors, see U.S. application Ser. Nos 11/258,401; 11/258,603; 11/258, 392 and 11/258,360 are incorporated herein by reference. Mesenchymal cells may be isolated by similar techniques or through the use of a gradient, such as FICOL gradient. Mesenchymal cells in a bone marrow sample will attach to surface, whereas other undesired cells will not attach and remain in the media. The media with the undesired cells is removed leaving the desired mesenchymal cells. The mesenchymal cells, as with other cells, are cultured, expanded, subjected to external biasing factors and/or genetically modified.

In the context of the present application, a polynucleotide sequence is "homologous" with the sequence according to the invention if at least 70%, preferably at least 80%, most preferably at least 90% of its base composition and base sequence corresponds to the sequence according to the invention. According to the invention, a "homologous protein" is to be understood to comprise proteins which contain an amino acid sequence at least 70% of which, preferably at least 80% of which, most preferably at least 90% of which, corresponds to a given amino acid sequence; wherein corresponds is to be understood to mean that the corresponding amino acids are either identical or are mutually homologous amino acids. The expression "homologous amino acids" denotes those which have corresponding properties, particularly with regard to their charge, hydrophobic character, steric properties, etc. Thus, in one embodiment the protein may be from 70% up to less than 100% homologous to nanog (SEQ ID NO. 2).

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The term "isolated" means separated from its natural environment.

The term "polynucleotide" refers in general to polyribonucleotides and polydeoxyribonucleotides, and can denote an unmodified RNA or DNA or a modified RNA or DNA.

The term "polypeptides" is to be understood to mean peptides or proteins which contain two or more amino acids which are bound via peptide bonds.

The polypeptides for use in accord with the teachings herein include polypeptides corresponding to nanog, and also includes those, at least 70% of which, preferably at least 80% of which, are homologous with the polypeptide corresponding to nanog, and most preferably those which exhibit a homology of least 90% to 95% with the polypeptide corresponding to nanog and which have dedifferentiating influence. Thus, the polypeptides may have a homology of from 70% to up to 100% with respect to SEQ ID NO. 2.

As used herein, a "polypeptide sequence exhibiting dedifferentiating influence" is a polypeptide whose presence in the cell causes an increase in potency, or transformation from a less developmentally potent cell to a more developmentally potent cell. Examples of such polypeptide sequences include the expression products of SEQ ID NO. 1, and polynucleotide sequences that hybridize to the complement of SEQ ID NO. 1, as well as expression products of the polynucleotide sequences listed in Table 1:

Table 1
Pem (mouse GI:1255173)
Fan Y, et al. Developmental Biology 210: 481-496. 1999
POU5F1 (Unigene Hs.2860)
Sox2 (Unigene Hs.816)
HESX1 (Unigene Hs.171980)
UTF1 (Unigene Hs.158307)
REX1 (Unigene Hs.335787)
FOXD3 (Unigene Hs.120204)
GBX2 (Unigene Hs.326290)
NANOG (Unigene Hs.326290)
LIN-28 (Unigene 86154)
TGIF
DNMT3A/B (251673)
TGFF1 (75561)
Richards M, et al. Stem Cells 22: 51-64. 2004
EGS-1 (accession # X57708.1)
FGF4 Tanaka T, et al. Genome Research 12: 1921-1928. 2002.
Rex-1 (accession # AF 4 5 0 4 5 4)

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the Tm can be approximated from the equation of Meinkoth and Wahl, Anal. Biochem., 138:267-284 (1984): Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Current Protocols in Molecular Biology, Chapter 2, Ausubel, et al., Eds., Greene Publishing and Wiley-Interscience, New York (2000).

Accordingly, polynucleotide sequences that hybridize to the complement of the sequence in SEQ ID NO. 1 are contemplated for use in dedifferentiating cells as taught herein.

According to another embodiment, the subject invention comprises a method of influencing transcription of an endogenous polynucleotide sequence comprising contacting a non-embryonic cell or cellular component comprising an endogenous polynucleotide sequence with a nanog protein or protein encoded by a polynucleotide sequence that hybridizes to a complement of SEQ ID NO. 1 under stringent conditions (i.e. nanog-like protein). Such influence may further include, but is not limited to, demethylation of DNA and reversal histone acetylation. The nanog protein or nanog-like protein may be one expressed by a polynucleotide sequence introduced in the cell or cellular component, or protein delivered into the cell or cellular component, or protein expressed by an endogenous polynucleotide sequence that has been activated. Nanog expression may be activated by the provision of Oct 4 and/or Sox2, which typically form a dimer. In a specific embodiment, the cellular component is a nucleus, liposome, or mitochondria. Such endogenous polynucleotide sequence or cellular component contacted by nanog or nanog may be removed from a cell or cellular component and introduced into another cell or cellular component.

Example 1

Stem Cell Bank System Embodiment

Figure 1:
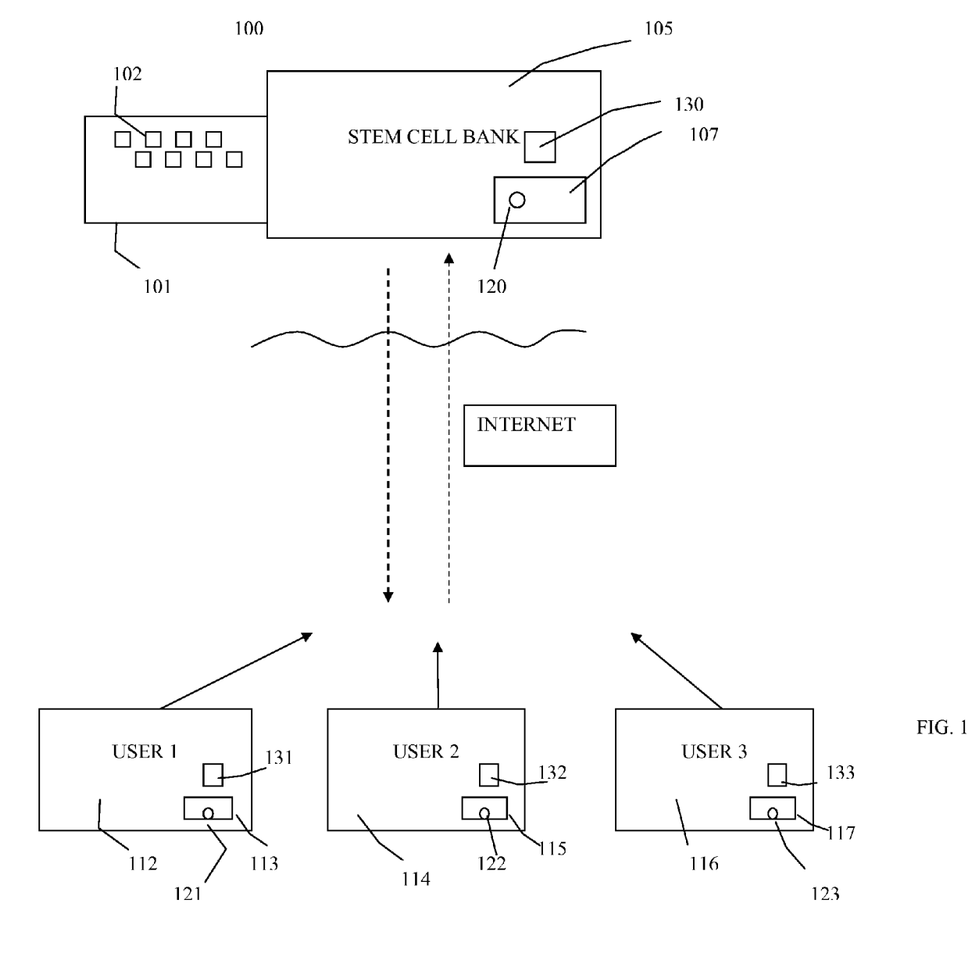
FIG. 1 shows a diagram of a stem cell banking system embodiment.

In one embodiment, as shown in FIG. 1, the subject invention relates to a stem cell banking system embodiment 100 comprising a stem cell bank 105. A plurality of stem cell populations are processed, such as by the method discussed in FIG. 2. In a specific embodiment, the stem cell populations 102 are stored in a housing facility 101 comprising the suitable freezing systems to maintain stem cells in a viable condition. Freezing systems may include but are not limited to a conventional freezer or a chamber holding a freezing medium such as liquid nitrogen, dry ice, frozen water, etc. The stem cell bank 105 maintains a stem cell database computer unit 107. Users 112, 114, 116 each having user computer units 113, 115, 117 that interface with database computer unit 107 via a network connection 109. Each computer unit comprises at least one processing module 120, 121, 122, and 123, respectively, for processing information. Furthermore, each computer unit is communicatingly connected to a display 130, 131, 132, and 133. Information directed to stem cell populations 102 are stored on database computer 107 which are conveyed to users 112, 114, 116 on user computer units 113, 115, and 117 via network connection, such as according to FIG. 3 as described in further detail below. The system provides the customer the ability to evaluate stem cell populations to determine which are suitable for their ongoing research and facilitates the transaction of purchasing stem cells and proper shipment.

As will be appreciated by one of skill in the art, embodiments of the present invention may be embodied as a device or system comprising a processing module, and/or computer program product comprising at least one program code module. Accordingly, the present invention may take the form of an entirely hardware embodiment or an embodiment combining software and hardware aspects. Furthermore, the present invention may include a computer program product on a computer-usable storage medium having computer-usable program code means embodied in the medium. Any suitable computer readable medium may be utilized including hard disks, CD-ROMs, DVDs, optical storage devices, or magnetic storage devices.

The term "processing module" may include a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The processing module may have operationally coupled thereto, or integrated therewith, a memory device. The memory device may be a single memory device or a plurality of memory devices. Such a memory device may be a read-only memory, random access memory, volatile memory, non-volatile memory, static memory, dynamic memory, flash memory, and/or any device that stores digital information. A computer, as used herein, is a device that comprises at least one processing module, and optionally at least one memory device.

The computer-usable or computer-readable medium may be or include, for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM), a CD ROM, a DVD (digital video disk), or other electronic storage medium. Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of certain embodiments of the present invention may be written in an object oriented and/or conventional procedural programming languages including, but not limited to, Java, Smalltalk, Perl, Python, Ruby, Lisp, PHP, "C", FORTRAN, or C++. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

Certain embodiments of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer-readable program code modules. These program code modules may be provided to a processing module of a general purpose computer, special purpose computer, embedded processor or other programmable data processing apparatus to produce a machine, such that the program code modules, which execute via the processing module of the computer or other programmable data processing apparatus, create means for implementing the functions specified in the flowchart and/or block diagram block or blocks.

These computer program code modules may also be stored in a computer-readable memory that can direct a computer or other programmable data processing apparatus to function in a particular manner, such that the program code modules stored in the computer-readable memory produce an article of manufacture.

The computer program code modules may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

Example 2

Harvesting and Processing of Stem Cells

Figure 2:
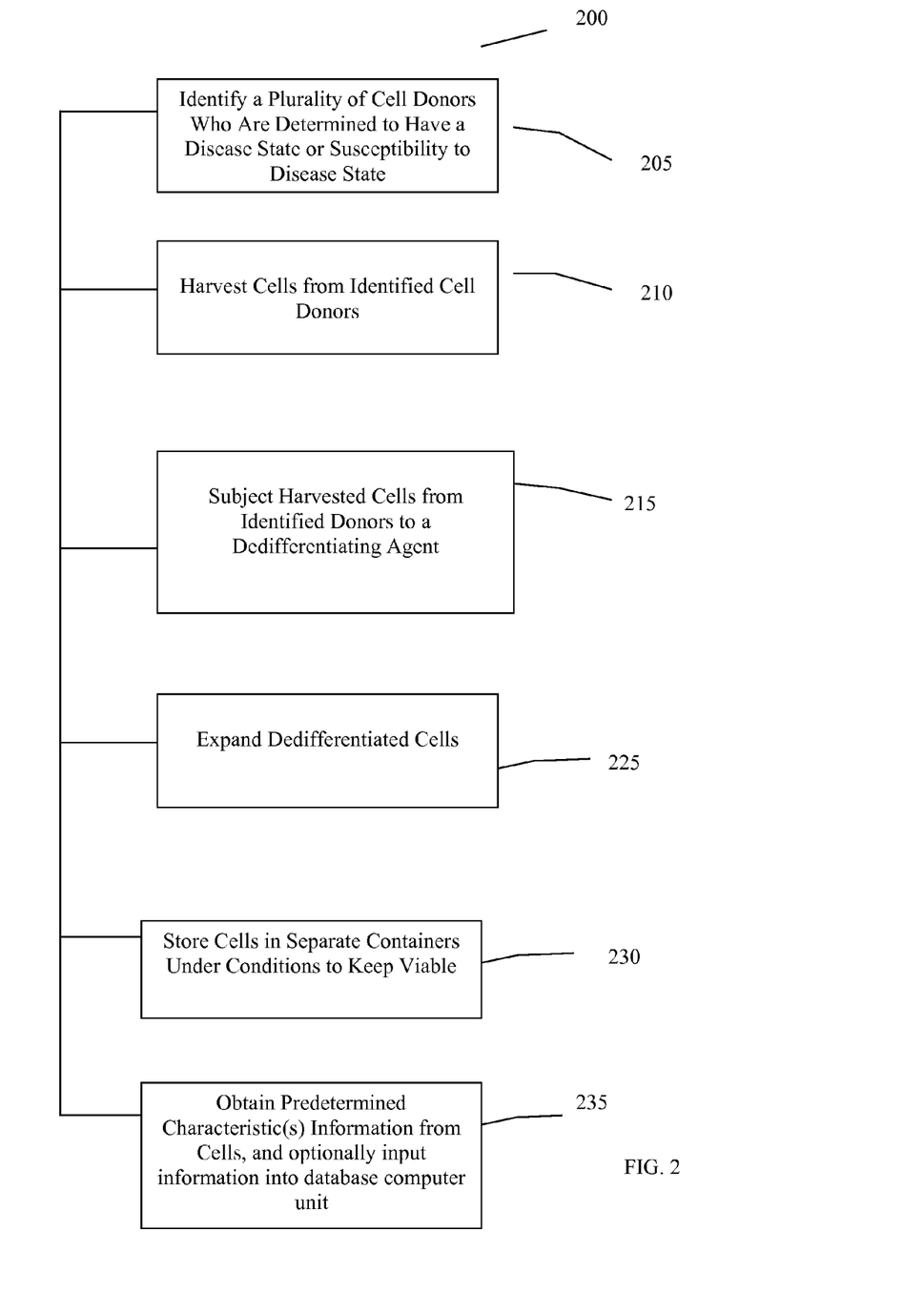
FIG. 2 shows a flow diagram of a method embodiment for producing a stem cell bank.

FIG. 2 illustrates one embodiment 200 of a method for harvesting and processing of stem cells for production of a stem cell bank. A plurality of cell donors are identified 205. In certain embodiments, donors are chosen due to the presence of a certain genetic profile and/or disease condition. Cells are harvested from individual donors 210. Numerous cell types may be suitable for harvesting including, including, but not limited to the cells types described above. Harvested stem cells are dedifferentiated 215. This may be achieved by a number of different methods as discussed above. Dedifferentiated stem cells are expanded 225 and then stored under conditions to keep them viable 230. Cells at any of steps 210, 215, 225, or 230 are studied to obtain information concerning predetermined characteristics, and such information is optionally inputted into a database computer unit, such as that described in FIG. 1.

Figure 3:
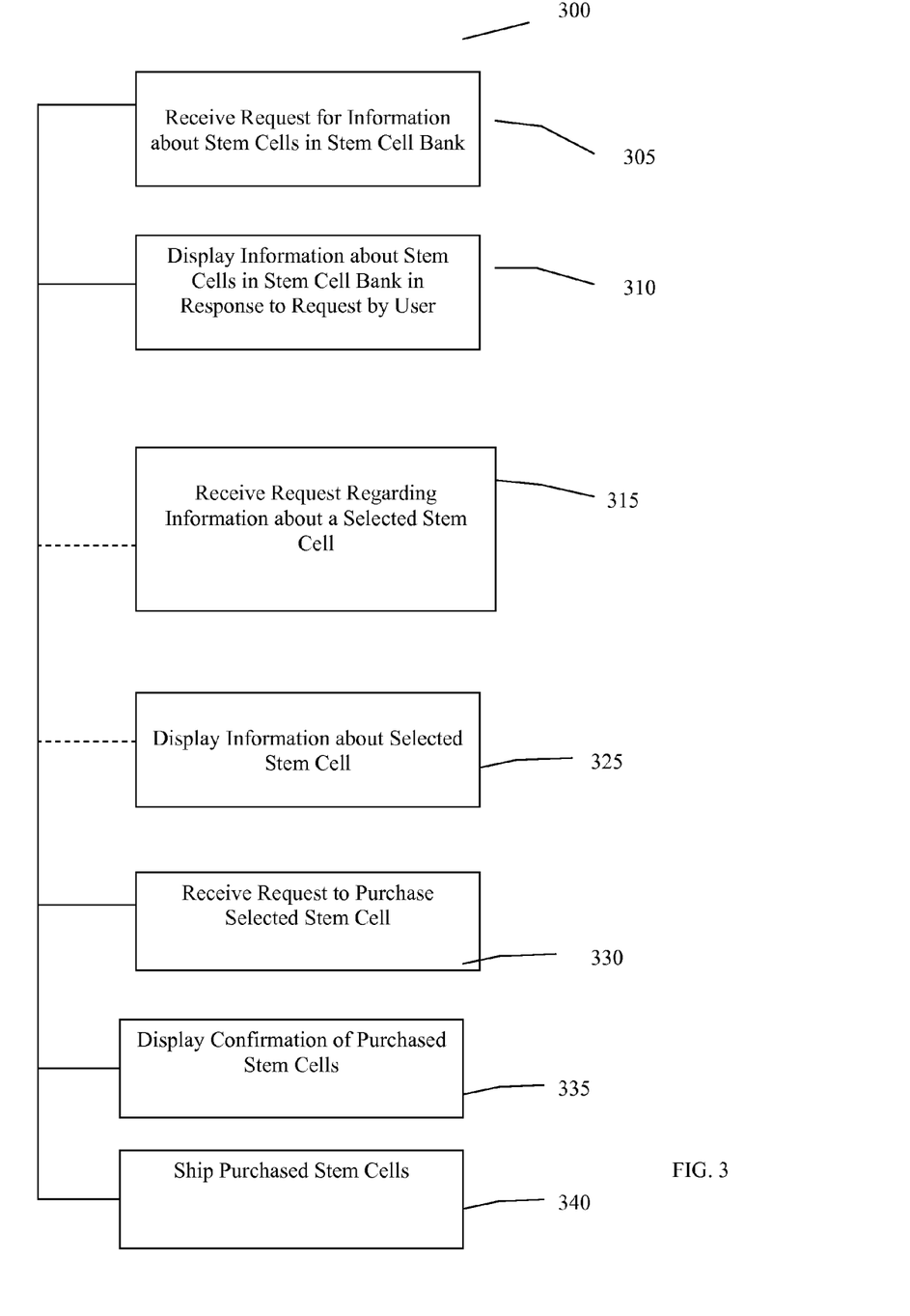
FIG. 3 shows a flow diagram of a method embodiment for providing for purchase of stem cell samples.

FIG. 3 describes a method embodiment 300 for providing information about cells at a stem cell bank, such information being previously inputted into a database computer unit and made available to users on a network, and to provide for purchase of stem cells. A request is received from a user to obtain information about stem cells 305, such as a request to determine availability of a stem cell sample correlating to certain keywords, and information is displayed to user regarding one or more stem cells 310, such as stem cells most closely matching keyword criteria. Providing an indication that no stem cells match the keyword criteria is also contemplated in an alternate embodiment. Furthermore, optionally, upon listing one or more stem cells most closely matching keyword criteria, a request for more detailed information about specific selected stem cell population(s) is received 315 and more detailed information concerning such selected population(s) is displayed to user. A request from User to purchase selected stem cells is received 330 and a confirmation of purchase is sent to the user 335. Purchased stem cells may then be shipped to customer and the shipping address provided by user 340.

Example 3

Methods of Using Identified Stem Cell Populations

As discussed above, the stem cells of the stem cell bank have increased potency which allows for their implementation in the same types of toxicology studies that are conducted with embryonic stem cells. See, for example, U.S. Patent Publication Nos. 20020045179 and 20020012905; as well as Toxicological Sciences 79, 214-223 (2004) which is itself and the references its cites incorporated herein by way of support for various toxicology studies for which the stem cell banking system can be used. The following references cited in the 2004 paper are particularly helpful:

Genschow, E., Scholz, G., Brown, N., Piersma, A., Brady, M., Clemann, N., Huuskonen, H., Paillard, F., Bremer, S., Becker, K., and Spielmann, H. (2000). Development of prediction models for three in vitro embryotoxicity tests in an ECVAM validation study. *In Vitro Mol. Tox.* 13, 51-65.

Rohwedel, J., Guan, K., Hegert, C., and Wobus, A. M. (2001). Embryonic stem cells as an in vitro model for mutagenicity, cytotoxicity and embryotoxicity studies: present state and future prospects. *Tox. in Vitro* 15, 741-753

Kehat, I., Kenyagin-Karsenti, D., Snir, M., Segev, H., Amit, M., Gepstein, A. S., Livne, E., Binah, O., Itskovitz-Eldor, J., and Gepstein, L. (2001). Human embryonic stem cells can differentiate into myocytes with structural and functional properties of cardiomyocytes. *J. Clin. Invest.* 108, 407-414.

Scholz, G., Genschow, E., Pohl, I., Bremer, S., Paparella, M., and Raabe, H. (1999). Prevalidation of the embryonic stem cell test EST—A new in vitro embryotoxicity test. *Toxicol In Vitro* 13, 675-681.

Kehat, I., Gepstein, A., Spira, A., Iskovitz-Eldor, J., and Gepstein, L. (2002). High-resolution electrophysiological assessment of human embryonic stem cell-derived cardiomyocytes. *Circ. Res.* 91, 659-661.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

U.S. Pat. Nos. 5,993,387; 6,493,724 and 6,640,211 are cited to for background information about sample banking systems. The teachings of all references cited herein are incorporated by reference in their entirety to the extent not inconsistent with the teachings herein.

What is claimed is:

1. A method of producing multiple stem cell populations for storage in a stem cell bank comprising:
    obtaining mesenchymal stem cells (MeSCs) from a subject;
    dedifferentiating said MeSCs by introducing into said MeSCs an expression cassette that expresses nanog internally to thereby increase developmental potency of said MeSCs;
    expanding said MeSCs; and
    cataloguing said MeSCs according to at least one predetermined characteristic;
wherein said at least one predetermined characteristic comprises morphological characteristics, differentiation profile, blood type, major histocompatibility complex, disease state of donor, or single nucleated polymorphisms a specific nucleic acid sequence associated with a gene, or genomic or mitochondrial DNA.

2. The method of claim 1, further comprising storing said cell populations under conditions to keep said cell populations viable.

3. The method of claim 2, wherein said storing comprises placing said cell populations in separate containers under freezing conditions.

4. The method of claim 1, wherein said cataloguing comprises inputting information about said predetermined characteristic of a given cell population into a database computer.

5. The method of claim 4, wherein said predetermined characteristic comprises disease state information of a donor.

6. The method of claim 1, wherein said predetermined characteristic comprises disease state information of donor.

7. A stem cell bank comprising:
    stem cell populations produced by the method of claim 1 and possessed by a single provider, wherein said stem cell populations comprise cells having an expression cassette comprising a nanog gene; and
    a catalogue comprising information of predetermined characteristic information correlating with said stem cell populations, wherein said predetermined characteristic information comprises morphological characteristics, differentiation profile, blood type, major histocompatibility complex, disease state of donor, or single nucleated polymorphisms a specific nucleic acid sequence associated with a gene, or genomic or mitochondrial DNA.

8. The stem cell bank of claim 7, wherein said catalogue is at least one database computer unit comprising at least one processing module and at least one memory device into which predetermined characteristic information of said multiple cell populations is inputted, and at least one program code module that causes predetermined characteristic information to be displayed onto a display which is in communication with said database computer.

9. The stem cell bank of claim 7, further comprising at least one freezer, wherein said stem cell populations are disposed within said at least one freezer.

10. The stem cell bank of claim 9, wherein said at least one freezer is in a building.

11. The stem cell bank of claim 7, wherein said multiple stem cell populations are individually placed within separate containers.

12. A stem cell banking system for storage and making available for purchase of stem cell populations comprising:
- at least one freezer;
- multiple stem cell populations produced by the method of claim 1 placed within said at least one freezer to produce stored stem cell populations, wherein said stem cell populations comprise cells having an expression cassette comprising a nanog gene; and
- at least one database computer unit comprising at least one processing module and at least one memory device into which predetermined characteristic information of said multiple cell populations is inputted, and a computer program product stored on said at least one memory device, said computer program product comprising program code modules that causes said database computer to:
- receive a request for information from a user computer unit onto a display which is in communication with said database about said stored stem populations;
- display information onto said display about stem cells in response to said request;
- display field to indicate intent to purchase at least one stem cell sample; and
- display confirmation of purchase of stem cells upon receiving a purchase indication.

* * * * *

SEQUENCE LISTING

```
<160> NUMBER OF SEQ ID NOS: 2

<210> SEQ ID NO 1
<211> LENGTH: 1628
<212> TYPE: DNA
<213> ORGANISM: Homo sapiens
<220> FEATURE:
<221> NAME/KEY: CDS
<222> LOCATION: (28)..(945)

<400> SEQUENCE: 1
tttttcctcc tcttcctcta tactaac atg agt gtg gat cca gct tgt ccc caa      54
                                Met Ser Val Asp Pro Ala Cys Pro Gln
                                 1               5 agc ttg cct tgc ttt gaa gaa tcc gac tgt aaa gaa tct tca cct atg       102
Ser Leu Pro Cys Phe Glu Glu Ser Asp Cys Lys Glu Ser Ser Pro Met
 10              15                  20                  25 cct gtg att tgt ggg cct gaa gaa aac tat cca tcc ttg caa atg tct       150
Pro Val Ile Cys Gly Pro Glu Glu Asn Tyr Pro Ser Leu Gln Met Ser
                 30                  35                  40 tct gct gag atg cct cac aca gag act gtc tct cct ctt cct tcc tcc       198
Ser Ala Glu Met Pro His Thr Glu Thr Val Ser Pro Leu Pro Ser Ser
             45                  50                  55 atg gat ctg ctt att cag gac agc cct gat tct tcc acc agt ccc aaa       246
Met Asp Leu Leu Ile Gln Asp Ser Pro Asp Ser Ser Thr Ser Pro Lys
         60                  65                  70 ggc aaa caa ccc act tct gca gag aat agt gtc gca aaa aag gaa gac       294
Gly Lys Gln Pro Thr Ser Ala Glu Asn Ser Val Ala Lys Lys Glu Asp
 75                  80                  85 aag gtc ccg gtc aag aaa cag aag acc aga act gtg ttc tct tcc acc       342
Lys Val Pro Val Lys Lys Gln Lys Thr Arg Thr Val Phe Ser Ser Thr
 90                  95                 100                 105 cag ctg tgt gta ctc aat gat aga ttt cag aga cag aaa tac ctc agc       390
Gln Leu Cys Val Leu Asn Asp Arg Phe Gln Arg Gln Lys Tyr Leu Ser
                110                 115                 120 ctc cag cag atg caa gaa ctc tcc aac atc ctg aac ctc agc tac aaa       438
Leu Gln Gln Met Gln Glu Leu Ser Asn Ile Leu Asn Leu Ser Tyr Lys
            125                 130                 135 cag gtg aag acc tgg ttc cag aac cag aga atg aaa tct aag agg tgg       486
Gln Val Lys Thr Trp Phe Gln Asn Gln Arg Met Lys Ser Lys Arg Trp
        140                 145                 150 cag aaa aac aac tgg ccg aag aat agc aat ggt gtg acg cag aag gcc       534
Gln Lys Asn Asn Trp Pro Lys Asn Ser Asn Gly Val Thr Gln Lys Ala
    155                 160                 165 tca gca cct acc tac ccc agc ctc tac tct tcc tac cac cag gga tgc       582
Ser Ala Pro Thr Tyr Pro Ser Leu Tyr Ser Ser Tyr His Gln Gly Cys
170                 175                 180                 185 ctg gtg aac ccg act ggg aac ctt cca atg tgg agc aac cag acc tgg       630
Leu Val Asn Pro Thr Gly Asn Leu Pro Met Trp Ser Asn Gln Thr Trp
```

```
                 190                 195                 200
aac aat tca acc tgg agc aac cag acc cag aac atc cag tcc tgg agc        678
Asn Asn Ser Thr Trp Ser Asn Gln Thr Gln Asn Ile Gln Ser Trp Ser
            205                 210                 215 aac cac tcc tgg aac act cag acc tgg tgc acc caa tcc tgg aac aat        726
Asn His Ser Trp Asn Thr Gln Thr Trp Cys Thr Gln Ser Trp Asn Asn
        220                 225                 230 cag gcc tgg aac agt ccc ttc tat aac tgt gga gag gaa tct ctg cag        774
Gln Ala Trp Asn Ser Pro Phe Tyr Asn Cys Gly Glu Glu Ser Leu Gln
    235                 240                 245 tcc tgc atg cac ttc cag cca aat tct cct gcc agt gac ttg gag gct        822
Ser Cys Met His Phe Gln Pro Asn Ser Pro Ala Ser Asp Leu Glu Ala
250                 255                 260                 265 gcc ttg gaa gct gct ggg gaa ggc ctt aat gta ata cag cag acc act        870
Ala Leu Glu Ala Ala Gly Glu Gly Leu Asn Val Ile Gln Gln Thr Thr
                270                 275                 280 agg tat ttt agt act cca caa acc atg gat tta ttc cta aac tac tcc        918
Arg Tyr Phe Ser Thr Pro Gln Thr Met Asp Leu Phe Leu Asn Tyr Ser
            285                 290                 295 atg aac atg caa cct gaa gac gtg tga agatgagtga aactgatatt              965
Met Asn Met Gln Pro Glu Asp Val
            300                 305 actcaatttc agtctggaca ctggctgaat ccttcctctc ccctcctccc atccctcata     1025 ggattttttct tgtttggaaa ccacgtgttc tggtttccat gatgcctatc cagtcaatct    1085
catggagggt ggagtatggt tggagcctaa tcagcgaggt ttcttttttt tttttttccta    1145 ttggatcttc ctggagaaaa tactttttttt tttttttttg agacggagtc ttgctctgtc    1205
gcccaggctg gagtgcagtg gcgcggtctt ggctcactgc aagctccgcc tcccgggttc    1265
acgccattct cctgcctcag cctcccgagc agctgggact acaggcgccc gccacctcgc    1325
ccggctaata ttttgtattt ttagtagaga cagggtttca ctgtgttagc caggatggtc     1385
tcgatctcct gaccttgtga tccgcccgcc tcggcctccc taacagctgg gattacaggc     1445
gtgagccacc gcgccctgcc tagaaaagac attttaataa ccttggctgc taaggacaac     1505
attgatagaa gccgtctctg gctatagata agtagatcta atactagttt ggatatcttt     1565
agggtttaga atctaacctc aagaataaga aatacaagta cgaattggtg atgaagatgt     1625
att                                                                  1628

<210> SEQ ID NO 2
<211> LENGTH: 305
<212> TYPE: PRT
<213> ORGANISM: Homo sapiens

<400> SEQUENCE: 2

Met Ser Val Asp Pro Ala Cys Pro Gln Ser Leu Pro Cys Phe Glu Glu
  1               5                  10                  15

Ser Asp Cys Lys Glu Ser Ser Pro Met Pro Val Ile Cys Gly Pro Glu
             20                  25                  30

Glu Asn Tyr Pro Ser Leu Gln Met Ser Ser Ala Glu Met Pro His Thr
         35                  40                  45

Glu Thr Val Ser Pro Leu Pro Ser Ser Met Asp Leu Leu Ile Gln Asp
     50                  55                  60

Ser Pro Asp Ser Ser Thr Ser Pro Lys Gly Lys Gln Pro Thr Ser Ala
 65                  70                  75                  80

Glu Asn Ser Val Ala Lys Lys Glu Asp Lys Val Pro Val Lys Lys Gln
                 85                  90                  95
```

-continued

```
Lys Thr Arg Thr Val Phe Ser Ser Thr Gln Leu Cys Val Leu Asn Asp
            100                 105                 110
Arg Phe Gln Arg Gln Lys Tyr Leu Ser Leu Gln Gln Met Gln Glu Leu
            115                 120                 125
Ser Asn Ile Leu Asn Leu Ser Tyr Lys Gln Val Lys Thr Trp Phe Gln
130                 135                 140
Asn Gln Arg Met Lys Ser Lys Arg Trp Gln Lys Asn Asn Trp Pro Lys
145                 150                 155                 160
Asn Ser Asn Gly Val Thr Gln Lys Ala Ser Ala Pro Thr Tyr Pro Ser
                165                 170                 175
Leu Tyr Ser Ser Tyr His Gln Gly Cys Leu Val Asn Pro Thr Gly Asn
            180                 185                 190
Leu Pro Met Trp Ser Asn Gln Thr Trp Asn Asn Ser Thr Trp Ser Asn
            195                 200                 205
Gln Thr Gln Asn Ile Gln Ser Trp Ser Asn His Ser Trp Asn Thr Gln
            210                 215                 220
Thr Trp Cys Thr Gln Ser Trp Asn Asn Gln Ala Trp Asn Ser Pro Phe
225                 230                 235                 240
Tyr Asn Cys Gly Glu Glu Ser Leu Gln Ser Cys Met His Phe Gln Pro
                245                 250                 255
Asn Ser Pro Ala Ser Asp Leu Glu Ala Ala Leu Glu Ala Ala Gly Glu
            260                 265                 270
Gly Leu Asn Val Ile Gln Gln Thr Thr Arg Tyr Phe Ser Thr Pro Gln
            275                 280                 285
Thr Met Asp Leu Phe Leu Asn Tyr Ser Met Asn Met Gln Pro Glu Asp
            290                 295                 300
Val
305
```